United States Patent [19]

Kawaguchi et al.

[11] Patent Number: 5,206,261
[45] Date of Patent: Apr. 27, 1993

[54] OXINDOLE DERIVATIVE

[75] Inventors: Akihiro Kawaguchi, Honjo; Atsushi Sato; Makoto Kajitani, both of Saitama; Mitsugi Yasumoto, Honjo; Junji Yamamoto, Tokushima, all of Japan

[73] Assignee: Taiho Pharmaceutical Company, Limited, Tokyo, Japan

[21] Appl. No.: 663,960

[22] PCT Filed: Jul. 23, 1990

[86] PCT No.: PCT/JP90/00945

§ 371 Date: Mar. 20, 1991

§ 102(e) Date: Mar. 20, 1991

[87] PCT Pub. No.: WO91/01306

PCT Pub. Date: Feb. 7, 1991

[30] Foreign Application Priority Data

Jul. 25, 1989 [JP] Japan .................. 1-191822

[51] Int. Cl.$^5$ .................. C07D 209/34; A01K 31/40
[52] U.S. Cl. .................. 514/418; 514/339; 546/273; 548/486
[58] Field of Search .................. 548/486; 546/273; 514/339, 418

[56] References Cited

FOREIGN PATENT DOCUMENTS 57-179158 11/1982 Japan .

OTHER PUBLICATIONS

Coda, J. Chem. Res. Synop (3) 84 (1986).

Primary Examiner—Robert Gerstl
Attorney, Agent, or Firm—Nikaido, Marmelstein, Murray & Oram

[57] ABSTRACT

The present invention provides an oxindole derivative which has the following formula and is useful as medicaments for treating senile dementia, i.e., as cerebral function improving agents and cerebral metabolism activators or anoxic brain damage protectives

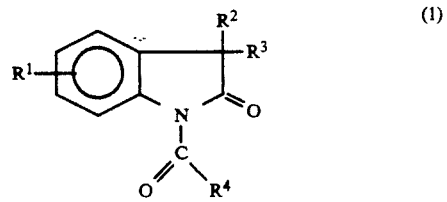

wherein $R^1$ is hydrogen atom, halogen atom, lower alkyl group or lower alkoxyl group, $R^2$ is hydrogen atom or lower alkyl group, $R^3$ is —$CH_2$—$R^5$ group ($R^5$ being alkyl group which may form a ring; benzodioxanyl group; or phenyl group which may have plural substituents selected from among halogen atom, lower alkyl group, lower alkoxyl group, hydroxyl group, diethylamino group, trifluoromethyl group, nitrile group, nitro group and benzyloxy group), $R^2$ and $R^3$ may form together =CH—$R^5$ ($R^5$ being same as above), $R^4$ is 1-propylbutyl group; pyridyl group; or phenyl group which may be substituted by lower alkoxyl group, halogen atom, diethylamino group, benzyloxy group, trifluoromethyl group, nitrile group, nitro group or lower alkyl group.

7 Claims, No Drawings

OXINDOLE DERIVATIVE

TECHNICAL FIELD

The present invention relates to a novel oxindole derivative. The present compound has cerebral function improving effect, cerebral metabolism activating or anoxic brain damage protecting effect and effect against senile dementia.

BACKGROUND ART

With an increase in the population of advanced ages in recent years, patients with senile dementia increase in number, posing a serious problem medically and socially. Although various antidementia drugs have been investigated and developed in view of the situation, no compounds have been provided with satisfactory efficacy. It has been strongly desired to develop medicaments for treating the disease.

An object of the present invention is to provide novel oxindole derivatives which are very useful as medicaments for treating senile dementia, i.e., as cerebral function improving agents and cerebral metabolism activators or anoxic brain damage protectives.

DISCLOSURE OF THE INVENTION

The present invention provides an oxindole derivative represented by the formula

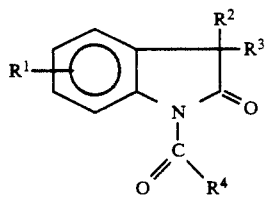

(1)

wherein $R^1$ is hydrogen atom, halogen atom, lower alkyl group or lower alkoxyl group, $R^2$ is hydrogen atom or lower alkyl group, $R^3$ is —$CH_2$—$R^5$ group ($R^5$ being alkyl group which may form a ring; benzodioxanyl group; or phenyl group which may have plural substituents selected from among halogen atom, lower alkyl group, lower alkoxyl group, hydroxyl group, diethylamino group, trifluoromethyl group, cyano group, nitro group and benzyloxy group), $R^2$ and $R^3$ may form together =CH—$R^5$ ($R^5$ being same as above), $R^4$ is 1-propylbutyl group; pyridyl group; or phenyl group which may be substituted by lower alkoxyl group, halogen atom, diethylamino group, benzyloxy group, trifluoromethyl group, cyano group, nitro group or lower alkyl group.

In the invention, examples of lower alkyl groups represented by $R^1$, $R^2$, $R^4$ and $R^5$ are preferably a straight-chain or branched-chain alkyl group having 1 to 6 carbon atoms such as methyl, ethyl, n-propyl, isopropyl, n-butyl, isobutyl, sec-butyl, tert-butyl, pentyl, isopentyl and hexyl group. Examples of halogen atoms represented by $R^1$, $R^4$ and $R^5$ are fluorine, chlorine, bromine and iodine. Examples of lower alkoxyl groups represented by $R^1$, $R^4$ and $R^5$ are preferably a straight-chain or branched-chain alkoxyl group having 1 to 6 carbon atoms such as methoxy, ethoxy, n-propoxy, isopropoxy, n-butoxy, isobutoxy, sec-butoxy, tert-butoxy, pentyloxy, isopentyloxy and hexyloxy group. Examples of alkyl groups which may form a ring and represented by $R^5$ are preferably the above lower alkyl groups and cycloalkyl groups having 3 to 6 carbon atoms such as cyclopropyl, cyclobutyl, cyclopentyl and cyclohexyl group.

When $R^5$ of the above formula (1) is a substituted phenyl group, the group preferably has 1 to 3 substituents.

Among the compounds of the formula (1), preferable are those wherein $R^1$ is hydrogen atom or lower alkoxyl group, $R^2$ is hydrogen atom, $R^3$ is —$CH_2$—$R^5$ group ($R^5$ being phenyl group which may have plural substituents selected from among halogen atom, lower alkyl group, lower alkoxyl group, hydroxyl group and diethylamino group), $R^4$ is 1-propylbutyl group, pyridyl group or phenyl group which may have plural lower alkoxyl groups as substituents. More preferable are those wherein $R^1$ and $R^2$ are each hydrogen atom, $R^3$ is —$CH_2$—$R^5$ group ($R^5$ being phenyl group substituted by 1 to 3 methoxy groups), $R^4$ is 4-methoxyphenyl group or phenyl group.

Further, we have found that the present compound of the formula (1) has an excellent cerebral function improving effect, cerebral metabolism activating or anoxic brain damage protecting effect and effect against senile dementia.

Accordingly, the present invention provides a cerebral function improving composition and a cerebral metabolism activating or anoxic brain damage protecting composition each comprising an effective amount of a compound of the formula (1) and a pharmacologically acceptable carrier.

The present invention further provides a method of improving cerebral functions and activating cerebral metabolism or protecting anoxic brain damage characterized by administering an effective amount of a compound of the formula (1).

The compounds of the formula (1) have pharmacological activities to ameliorate:

(1) cerebral damage in anoxia, and
(2) amnesia induced by scopolamine in passive condition avoidance response.

These pharmacological properties are useful for activating injured nervous cells and ameliorate memory and learning disturbances.

Accordingly, the compounds of the present invention are usable not only as medicaments for use in treating deterioration of intelligence or neurasthenia, amnesia, senile dementia or intellectual fatigue, cerebrovascular dementia, aftereffects of encephalopathy and Alzheimer's disease but also as medicaments for improving other cerebral functions or for activating cerebral metabolism or protecting anoxic brain damage.

The oxindole derivative (1) of the present invention can be prepared, for example, by the following reaction processes.

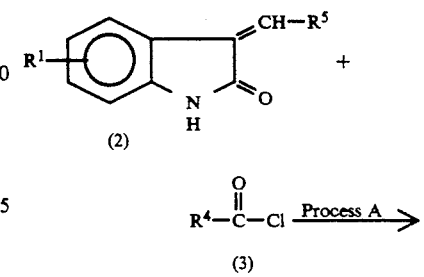

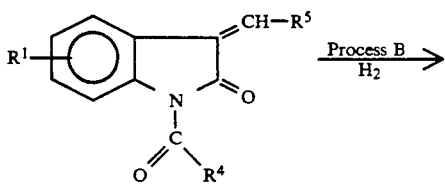

(1a)

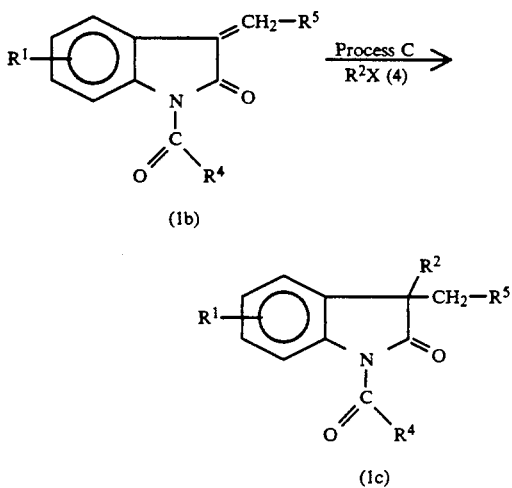

(1b)

(1c)

wherein $R^1$, $R^2$, $R^4$ and $R^5$ are as defined above, X is halogen atom.

Process A

The present compound of the formula (1a) can be prepared by reacting the acid chloride derivative (3) with the known oxindole compound (2) [A. C. Code et al, Journal of Chemical Society. Perkin Transactions II, 615 (1984)], in the presence of a base in an appropriate solvent.

The solvent is not limited specifically insofar as it does not participate in the reaction. Examples of solvents generally useful are hydrocarbon halides such as dichloromethane and chloroform, ethers such as ethyl ether and tetrahydrofuran, aromatic hydrocarbons such as benzene and toluene, aprotic polar solvents such as N,N-dimethylformamide and dimethylsulfoxide.

As to the proportion of the compound (2) and the acid chloride derivative (3), it is usual to use 0.5 to 2 moles, preferably one mole of the compound (3) per mole of the compound (2). Examples of bases are organic amines such as triethylamine, pyridine and 4-dimethylaminopyridine, and inorganic bases such as sodium hydride and sodium amide. The amount of the base is usually 0.5 to 2 moles, preferably one mole per mole of the compound (2). The reaction temperature is 0° to 150° C., preferably 50° to 100° C. The reaction time is 1 to 24 hours, preferably 2 to 10 hours.

Process B

The present compound of the formula (1b) can be prepared by hydrogenating the compound (1a) obtained in the above Process A, in the presence of a catalyst in an appropriate solvent.

The solvent is not limited specifically insofar as it does not participate in the reaction. Examples of solvents generally useful are alcohols such as methanol and ethanol, esters such as methyl acetate and ethyl acetate, aprotic polar solvents such as N,N-dimethylformamide and dimethylsulfoxide. The catalysts include 5 to 10% Pd-C, etc. The reaction temperature is 0° to 100° C., preferably 0° to 30° C. The reaction time is 0.5 to 24 hours, preferably 1 to 5 hours. The hydrogen pressure is 1 to 10 atm., preferably 2 to 5 atm.

Process C

The present compound of the formula (1c) can be prepared by reacting the compound (1b) obtained in the above Process B with the compound of the formula (4) in the presence of a base in an appropriate solvent.

The solvent is not limited specifically insofar as it does not participate in the reaction. Examples of solvents generally useful are ethers such as ethyl ether and tetrahydrofuran, aromatic hydrocarbons such as benzene and toluene, hydrocarbon halides such as dichloromethane and chloroform, aprotic polar solvents such as N,N-dimethylformamide and dimethylsulfoxide.

As to the proportion of the compound (1b) and the compound (4), it is usual to use 0.5 to 5 moles, preferably 1 to 2 moles of the compound (4) per mole of the compound (1b). Examples of bases are organic amines such as triethylamine and pyridine, and inorganic bases such as sodium hydride and potassium hydride. The amount of the base is usually 0.5 to 2 moles, preferably one mole per mole of the compound (1b). The reaction temperature is −50° to 100° C., preferably 0° to 30° C. The reaction time is 0.5 to 24 hours, preferably 1 to 6 hours.

The present compound can be readily purified or isolated by a usual separating method, such as extraction, distillation, recrystallization., gas or liquid column chromatography or the like.

When the present compound is to be administered for the purpose of treating deterioration of intelligence or neurasthenia, amnesia, senile dementia or intellectual fatigue, and Alzheimer's disease, the compound is administered in the form of a pharmacological preparation such as oral preparation, injection, suppository or the like. These preparations can be produced by conventional methods already known to those skilled in the art.

Solid preparations for oral administration can be produced in a usual manner by adding to the present compound an excipient, and when required, a binder, disintegrator, lubricant, coloring agent, corrigent, flavor and the like, and making the mixture into tablets, granules, powders or an encapsulated preparation. Such additives are those generally used in the art. Examples of useful excipients are lactose, sucrose, sodium chloride, glucose, starch, calcium carbonate, kaolin, microcrystalline cellulose, silicic acid and the like. Examples of useful binders are water, ethanol, propanol, syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like. Examples of useful disintegrators are dried starch, sodium alginate, agar powder, sodium hydrogencarbonate, calcium carbonate, sodium laurylsulfate, stearic acid monoglyceride, starch, lactose and the like. Examples of useful lubricants are purified talc, stearic acid salts, borax, polyethylene glycol and the like. Examples of useful corrigents are sucrose, bitter orange peel, citric acid, tartaric acid and the like.

Liquid preparations for oral administration can be produced by adding a corrigent, buffer, stabilizer, flavor and the like to the present compound, and making the mixture into a liquid oral preparation, syrup, elixir or the like. Examples of useful corrigents are those exemplified above. Exemplary of useful buffers are sodium citrate and the like. Examples of useful stabilizers are tragacanth, gum arabic, gelatin and the like.

Injections can be produced in a usual manner by adding a pH adjusting agent, buffer, stabilizer, isotonic agent, local anesthetic and the like to the present compound, and formulating the mixture into a preparation for subcutaneous, intramuscular or intravenous injection. Examples of useful pH adjusting agents and buffers are sodium citrate, sodium acetate, sodium phosphate and the like. Examples of useful stabilizers are sodium pyrosulfite, EDTA, thioglycolic acid, thiolactic acid and the like. Examples of useful local anesthetics are procaine hydrochloride, lidocaine hydrochloride and the like.

Suppositories can be prepared by adding to the present compound a pharmaceutical carrier known in the art, such as polyethylene glycol, lanolin, cacao fat, fatty acid triglyceride or the like, along with Tween (registered trademark) or like surfactant and the like when desired, and treating the mixture in the usual manner.

Although the amount of the present compound to be contained in the unit form of each preparation varies with the symptoms of the patient, the type of preparation, etc., the amount is generally preferably about 1 to about 300 mg for oral administration, about 1 to about 50 mg for injection or about 1 to 200 mg for suppositories, per unit of the preparation. The dosage of the compound to be given in the form of such a preparation can not be determined specifically but varies with the symptoms, weight, age, sex, etc. of the patient. However, it is given usually at a dose of about 0.5 to about 1000 mg, preferably 1 to 500 mg, per day for adults, preferably once or in up to four divided doses.

BEST MODE FOR CARRYING OUT THE INVENTION

The present invention will be described below in greater detail with reference to examples wherein oxindole derivatives of the formula (1) were prepared, and to the tests conducted to determine the antiamnesia activity of compounds (1) and the acute toxicity test thereof. Tables 1 and 2 show the compounds prepared in the examples. In the elementary analysis in the Table, upper column shows analyzed value, lower column calculated value.

EXAMPLE 1

To a solution of 5 g (22.6 mmole) of 3-benzylideneoxindole [A. C. Code et al, Journal of Chemical Society. Perkin Transactions II, 615 (1984)] and 3.2 g (22.6 mmol) of benzoyl chloride in 100 ml of dichloromethane was added dropwise 2.3 g (22.6 mmol) of triethylamine. The mixture was heated under reflux for 5 hours. The reaction solution, after cooled, was washed with water and 10% hydrochloric acid, and dried over anhydrous magnesium sulfate. After removing the solvent, the resulting yellow crystal was recrystallized from chloroform-ethyl acetate to give 7.1 g (yield 93%) of 1-benzoyl-3-benzylideneoxindole (Compound 36). Table 2 shows melting point and elementary analysis of the compound.

EXAMPLE 2

Compound 38 was obtained in the same manner as in Example 1 with use of, as a starting material, 3-(4-methoxybenzylidene)oxindole [A. C. Code et al, Journal of Chemical Society. Perkin Transactions II, 615 (1984)]. Table 2 shows melting point and elementary analysis of the compound.

EXAMPLE 3

To a solution of 5 g (19.9 mmole) of 3-(4-methoxybenzylidene)oxindole and 3.4 g (19.9 mmol) of 4-methoxybenzoyl chloride in 100 ml of dichloromethane was added dropwise 2.0 g (19.9 mmol) of triethylamine and a catalytic amount of 4-dimethylaminopyridine. The mixture was heated under reflux for 5 hours. The reaction solution, after cooled, was washed with water and 10% hydrochloric acid, and dried over anhydrous magnesium sulfate. After removing the solvent, the resulting yellow crystal was recrystallized from chloroform-ethyl acetate to give 6.6 g (yield 86%) of 1-(4-methoxybenzoyl)-3-(4-methoxybenzylidene)oxindole (Compound 39). Table 2 shows melting point and elementary analysis of the compound.

EXAMPLE 4

Compound 37 and 40 to 70 were obtained in the same manner as in Example 3 with use of, as a starting material, corresponding benzylideneoxindoles. Table 2 shows melting point and elementary analysis of the compounds. Table 3 gives $^1$H-NMR values of Compounds 51 to 53 and 66.

EXAMPLE 5

In 200 ml of ethyl acetate were suspended 3 g (8.9 mmol) of 1-benzoyl-3-benzylideneoxindole (Compound 36) obtained in Example 1 and 1 g of 10% Pd-C. The suspension was shaken at room temperature for 2 hours at a hydrogen pressure of 3 atm. The filtrate obtained by filtering 10% Pd-C was concentrated. The resulting residue was recrystallized from chloroform-methanol to give 2.5 g (yield 83%) of 1-benzoyl-3-benzyloxindole (Compound 1). Table 1 shows melting point and elementary analysis of the compound.

EXAMPLE 6

Compounds 2 to 12, 14 to 22, and 24 to 35 were obtained in the same manner as in Example 5 with use of, as a starting material, corresponding oxindole derivatives. Table 1 shows melting point and elementary analysis of the compounds. Table 3 gives $^1$H-NMR values of Compounds 18, 19, 21, 24, 25, 28, 30 and 34.

EXAMPLE 7

In 200 ml of ethyl acetate were suspended 5 g (11.3 mmol) of 1-(4-methoxybenzoyl)-3-(4-benzyloxybenzylidene)oxindole (Compound 14) obtained in Example 6, 1 g of 10% Pd-C and 0.5 ml of conc. hydrochloric acid. The suspension was shaken at room temperature for 2 hours at a hydrogen pressure of 3 atm. The filtrate obtained by filtering 10% Pd-C was concentrated. The resulting residue was recrystallized from chloroform-ethyl acetate-ethyl ether to give 3.1 g (yield 80%) of 1-(4-methoxybenzoyl)-3-(4-hydroxybenzyl)oxindole (Compound 13). Table 1 shows melting point and elementary analysis of the compound.

EXAMPLE 8

To a suspension of 187 mg (7.8 mmol) of sodium hydride in 20 ml of tetrahydrofuran was added dropwise under ice-cooling a solution of 3 g (7.8 mmole) of 1-(4-methoxybenzoyl)-3-(4-methoxybenzyl)oxindole (Compound 4) in 50 ml of tetrahydrofuran. The mixture was stirred for 30 minutes, 2.2 g (15.6 mmol) of methyl iodide was added dropwise thereto under ice-cooling, and the mixture was stirred at room temperature for 3 hours. To the reaction solution were added 10 ml of water and 30 ml of saturated aqueous solution of ammonium chloride. After stirred for 10 minutes, the mixture was extracted with ethyl acetate. The organic layer was dried over anhydrous magnesium sulfate and the solvent was removed. The residue was chromatographed over silica gel to obtain 2.7 g (yield 88%) of 1-(4-methoxybenzoyl)-3-methyl-3-(4-methoxybenzyl)oxindole (Compound 23) from hexane-ethyl acetate (4:1) elute. Table 1 shows elementary analysis and Table 3 shows $^1$H-NMR values of the compound.

In Tables 1 and 2, Me stands for methyl, Et ethyl, OMe methoxy, OEt ethoxy and OBn benzyloxy.

EXAMPLE 9

| | |
|---|---|
| Compound 4 | 200 mg |
| Lactose | 500 mg |
| Corn starch | 280 mg |
| Hydroxypropyl cellulose | 20 mg |

The above ingredients in the proportions given were made into a granular preparation by the usual method in an amount of 1000 mg per wrapper.

EXAMPLE 10

| | |
|---|---|
| Compound 7 | 100 mg |
| Lactose | 85 mg |
| Microcrystalline cellulose | 50 mg |
| Hydroxypropyl starch | 30 mg |
| Talc | 4 mg |
| Magnesium stearate | 1 mg |

By the usual method, the above ingredients in the proportions given were made into tablets each weighing 270 mg.

EXAMPLE 11

| | |
|---|---|
| Compound 53 | 100 mg |
| Lactose | 50 mg |
| Potato starch | 50 mg |
| Microcrystalline cellulose | 109 mg |
| Magnesium stearate | 1 mg |

By the usual method, the above ingredients in the proportions given were made into an encapsulated preparation in an amount of 310 mg in each capsule.

EXAMPLE 12

| | |
|---|---|
| Compound 3 | 250 mg |
| Fatty acid triglyceride | 750 mg |

By the usual method, the above ingredients in the proportions given were made into suppositories each weighing 1000 mg.

EXAMPLE 13

| | |
|---|---|
| Compound 2 | 5 mg |
| Sodium chloride | 18 mg |
| Distilled water for injections, suitable amount | |

The above ingredients in the proportions given were made into an injection by the usual method.

TEST EXAMPLE 1

Reversal Activity of Amnesia

1. Animals

Groups of 6 to 16 rats (Wistar, males, weighing 170 to 240 g) were used for the experiment.

2. Drug and Method of Administration

Scopolamine was used as dissolved in physiological saline, and the test compound as dissolved or suspended in 0.5% solution of sodium carboxymethyl cellulose.

Scopolamine was subcutaneously given at a dose of 0.5 mg/kg 30 minutes before aquisition trials. The test compound was orally given immediately after the aquisition trials.

3. Method

A step-through passive avoidance apparatus was used. The apparatus consisted of a dark compartment (25×12×30 cm) having a grid serving as a floor, and a light compartment (25×12×12 cm) illuminated with 20-W daylight fluorescent lamp from above and separated from the dark compartment by a guillotine door. The rat was subjected to habituation trials about 1 hour before aquisition trials. The habituation was accomplished by placing the rat into the light compartment, opening the door 5 seconds thereafter, closing the door when the four legs completely entered the dark compartment, leaving the rat in the dark compartment for 10 seconds and thereafter taking out the rat. The acquisition trial was accomplished in the same manner as the habituation 1 hour thereafter except that simultaneously when the door was closed upon the movement of the rat into the dark compartment, an unescapable foot shock of 4.5 mA was given to the rat by the floor grit for 1 second.

A retention test was conducted 24 hours after the aquisition trials to measure the step-through latency during which the rat placed into the light compartment remained therein before moving into the dark compartment, i.e., the duration of a passive avoidance reaction. For a rat exhibiting the avoidance reaction for more than a maximum period of time measured (300 seconds), 300 seconds was recorded.

The results were given by amnesia reversal (%) represented by the formula below which was described in J. Med. Chem. vol. 27 684~691 (1984).

$$\text{amnesia reversal (\%)} = \frac{\text{drug group} - \text{base-line control group}}{\text{ceiling control group} - \text{base-line control group}} \times 100$$

drug group: step-through latency (second) of the group administered with scopolamine and the test compound base-line control group: step-through latency (second) of the group administered with scopolamine ceiling control group: step-through latency (second) of the control group (max.; 300 seconds)

Table 4 shows the results in which Compounds 4, 7 and 53 were used. As a control was used Aniracetam which was investigated and considered effective in the present clinical fields. It is apparent from Table 4 that present compound exhibits excellent antiamnesia effect compared with Aniracetam in a dose of 1/10 to 1/30 of that of the latter.

TABLE 1

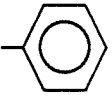

| No. | R¹ | R² | R⁵ | R⁴ | m.p. (°C.) | yield (%) | formula | C | H | N |
|---|---|---|---|---|---|---|---|---|---|---|
| 1 | H | H | 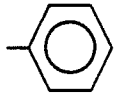 | 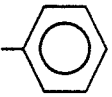 | 76~77 | 83 | $C_{22}H_{17}NO_2$ | 80.46 (80.71) | 5.51 (5.23) | 4.14 (4.28) |
| 2 | H | H | 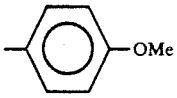 | 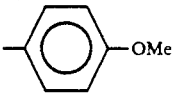—OMe | 106~107 | 85 | $C_{23}H_{19}NO_3$ | 77.31 (77.29) | 5.37 (5.36) | 3.80 (3.92) |
| 3 | H | H | 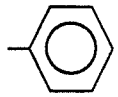—OMe | 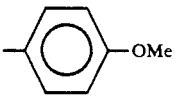 | 102–104 | 95 | $C_{23}H_{19}NO_3$ | 77.71 (77.29) | 5.53 (5.36) | 3.75 (3.92) |
| 4 | H | H | 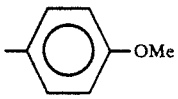—OMe | 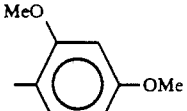—OMe | 115~116 | 98 | $C_{24}H_{21}NO_4$ | 74.40 (74.61) | 5.46 (5.56) | 3.62 (3.52) |
| 5 | H | H | 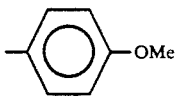 MeO, OMe | 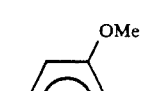—OMe | 102~104 | 92 | $C_{25}H_{23}NO_5$ | 71.89 (71.93) | 5.55 (5.55) | 3.23 (3.36) |
| 6 | H | H | 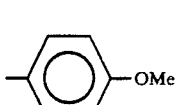 OMe, OMe | 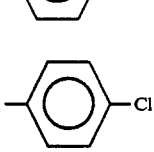—OMe | 130~133 | 90 | $C_{25}H_{23}NO_5$ | 72.24 (71.93) | 5.70 (5.55) | 3.22 (3.36) |
| 16 | H | H | 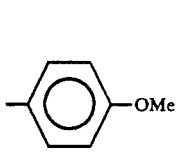—Cl | —OMe | 130~131 | 92 | $C_{23}H_{18}NO_3Cl$ | 70.69 (70.50) | 4.74 (4.63) | 3.47 (3.57) |
| 17 | H | H | —(CH₂)₅CH₃ | 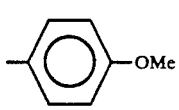—OMe | 60~61 | 90 | $C_{23}H_{27}NO_3$ | 75.53 (75.59) | 7.54 (7.45) | 3.73 (3.73) |
| 18 | H | H | 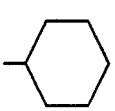 | —OMe | oil | 95 | $C_{23}H_{25}NO_3$ (¼ H₂O) | 74.90 (74.77) | 7.19 (7.00) | 3.50 (3.79) |
| 19 | H | H | 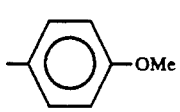—OMe | —CH(CH₂CH₂CH₃)₂ | oil | 85 | $C_{24}H_{29}NO_3$ | 75.76 (75.96) | 7.88 (7.70) | 3.58 (3.69) |

TABLE 1-continued

| No. | R¹ | R² | R⁵ | R⁴ | m.p. (°C.) | yield (%) | formula | C | H | N |
|---|---|---|---|---|---|---|---|---|---|---|
| 20 | 5-Cl | H | –C₆H₄–OMe | –C₆H₄–OMe | 97~98 | 90 | $C_{24}H_{20}NO_4Cl$ | 68.22 (68.33) | 4.76 (4.78) | 3.15 (3.22) |
| 21 | 5-Me | H | –C₆H₄–OMe | –C₆H₄–OMe | 45 | 95 | $C_{25}H_{23}NO_4$ | 73.10 (73.15) | 5.73 (5.89) | 3.32 (3.41) |
| 22 | 5-OMe | H | –C₆H₄–OMe | –C₆H₄–OMe | 101~103 | 88 | $C_{25}H_{23}NO_5$ | 72.10 (71.93) | 5.78 (5.55) | 3.20 (3.36) |
| 23 | H | Me | –C₆H₄–OMe | –C₆H₄–OMe | oil | 88 | $C_{25}H_{23}NO_4$ (1/5 $H_2O$) | 74.22 (74.13) | 6.12 (5.82) | 3.22 (3.46) |
| 24 | H | H | –C₆H₄–OMe | –C₆H₄–OMe (o-OMe) | oil | 96 | $C_{24}H_{21}NO_4$ | 74.26 (74.40) | 5.87 (5.46) | 3.37 (3.62) |
| 25 | H | H | –C₆H₄–OMe | –C₆H₄–Cl (o-Cl) | oil | 93 | $C_{23}H_{18}NO_3Cl$ | 70.47 (70.50) | 4.99 (4.63) | 3.50 (3.57) |
| 26 | H | H | –C₆H₄–OMe | –C₆H₄–OH | 193~193.5 | 90 | $C_{23}H_{19}NO_4$ | 73.81 (73.98) | 5.13 (5.13) | 3.55 (3.75) |
| 27 | H | H | –C₆H₄–OMe | –C₆H₄–CF₃ | 93~94 | 93 | $C_{24}H_{18}NO_3F_3$ (¼ $H_2O$) | 66.86 (66.82) | 4.46 (4.36) | 3.25 (3.20) |
| 28 | H | H | –C₆H₄–OMe | –pyridyl | oil | 90 | $C_{22}H_{18}N_2O_3$ (½ $H_2O$) | 71.25 (71.34) | 5.42 (5.26) | 7.49 (7.56) |
| 29 | H | H | –C₆H₄–OMe | –C₆H₄–CN | 56~57 (amorphous) | 93 | $C_{24}H_{18}N_2O_3$ (¼ $H_2O$) | 74.52 (74.50) | 5.11 (4.82) | 6.83 (7.24) |

TABLE 1-continued
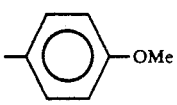
| No. | R¹ | R² | R⁵ | R⁴ | m.p. (°C.) | yield (%) | formula | C | H | N |
|---|---|---|---|---|---|---|---|---|---|---|
| 30 | H | H | 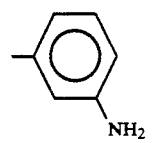 | 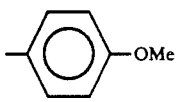 | oil | 90 | $C_{23}H_{20}N_2O_3$ ($H_2O$) | 70.70 (70.75) | 5.96 (5.68) | 6.71 (7.17) |
| 31 | H | H | 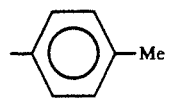 | 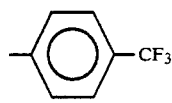 | 130.5~131 | 97 | $C_{24}H_{21}NO_3$ | 77.52 (77.61) | 5.80 (5.70) | 3.64 (3.77) |
| 32 | H | H | 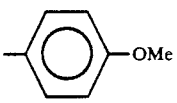 | 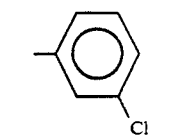 | 113~114 | 93 | $C_{24}H_{18}NO_3F_3$ | 67.83 (67.76) | 4.29 (4.26) | 3.23 (3.29) |
| 33 | H | H | 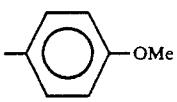 | 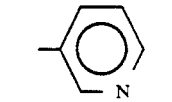 | 77~78 | 95 | $C_{23}H_{18}NO_3Cl$ | 70.55 (70.50) | 4.97 (4.63) | 3.45 (3.57) |
| 34 | H | H | 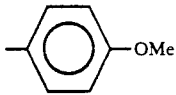 | 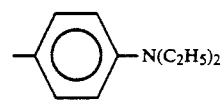 | oil | 90 | $C_{22}H_{18}N_2O_3$ | 70.85 (70.88) | 5.12 (5.30) | 7.27 (7.51) |
| 35 | H | H | 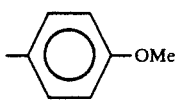 | 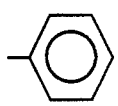 | 129~131 | 90 | $C_{27}H_{28}N_2O_3 \cdot HCl$ | 65.97 (65.91) | 6.47 (6.56) | 6.06 (5.69) |
TABLE 2
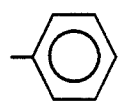
| No. | R¹ | R⁵ | R⁴ | m.p. (°C.) | yield (%) | formula | C | H | N |
|---|---|---|---|---|---|---|---|---|---|
| 36 | H | 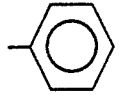 | 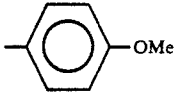 | 145~147 | 93 | $C_{22}H_{15}NO_2$ | 80.96 (81.21) | 4.65 (4.65) | 4.34 (4.30) |
| 37 | H | 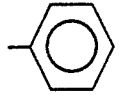 | 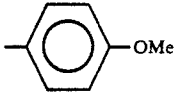 | 167.5 | 90 | $C_{23}H_{17}NO_3$ | 77.73 (77.73) | 4.77 (4.82) | 3.86 (3.94) |

TABLE 2-continued

Structure: 3-(=CHR⁵)-1-(C(=O)R⁴)-indolin-2-one with R¹ on benzene ring

| No. | R¹ | R⁵ | R⁴ | m.p. (°C.) | yield (%) | formula | C | H | N |
|---|---|---|---|---|---|---|---|---|---|
| 38 | H | 4-MeO-C₆H₄- | C₆H₅- | 146~147 | 93 | C₂₃H₁₇NO₃ (¼ H₂O) | 76.97 (76.76) | 4.85 (4.90) | 4.02 (3.89) |
| 39 | H | 4-MeO-C₆H₄- | 4-MeO-C₆H₄- | 174~175 | 86 | C₂₄H₁₉NO₄ | 74.59 (74.79) | 4.96 (4.97) | 3.45 (3.63) |
| 40 | H | 3,4-(MeO)₂-C₆H₃- | 4-MeO-C₆H₄- | 188~190 | 91 | C₂₅H₂₁NO₅ (1/6 H₂O) | 71.79 (71.76) | 5.03 (5.14) | 3.24 (3.35) |
| 41 | H | 2,3-(MeO)₂-C₆H₃- | 4-MeO-C₆H₄- | 162~164 | 95 | C₂₅H₂₁NO₅ | 72.31 (72.28) | 5.19 (5.09) | 3.23 (3.37) |
| 42 | H | 2,3,4-(MeO)₃-C₆H₂- | 4-MeO-C₆H₄- | 151~153 | 82 | C₂₆H₂₃NO₆ | 69.83 (70.10) | 5.23 (5.20) | 3.11 (3.14) |
| 43 | H | 3,4,5-(MeO)₃-C₆H₂- | 4-MeO-C₆H₄- | 167~168 | 83 | C₂₆H₂₃NO₆ | 70.06 (70.10) | 5.19 (5.20) | 3.00 (3.14) |
| 44 | H | 2,3,4-(MeO)₃-C₆H₂- | 4-MeO-C₆H₄- | 175~176 | 94 | C₂₆H₂₃NO₆ (¼ H₂O) | 69.15 (69.17) | 5.42 (5.28) | 3.19 (3.10) |
| 45 | H | 4-EtO-C₆H₄- | 4-MeO-C₆H₄- | 156~157 | 89 | C₂₅H₂₁NO₄ | 75.39 (75.17) | 5.33 (5.30) | 3.36 (3.51) |
| 46 | H | 2-EtO-C₆H₄- | 4-MeO-C₆H₄- | 171~172 | 89 | C₂₅H₂₁NO₄ (1/5 H₂O) | 74.48 (74.50) | 5.41 (5.35) | 3.60 (3.48) |

TABLE 2-continued
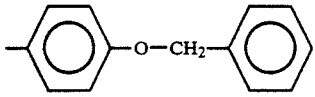
| No. | R¹ | R⁵ | R⁴ | m.p. (°C.) | yield (%) | formula | C | H | N |
|---|---|---|---|---|---|---|---|---|---|
| 47 | H | 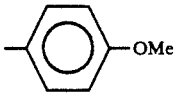 —O—CH₂— ⌬ | ⌬—OMe | 139~141 | 90 | $C_{30}H_{23}NO_4$ | 77.84 (78.08) | 5.08 (5.02) | 2.86 (2.87) |
| 48 | H | 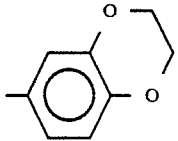 | ⌬—OMe | 188~190 | 95 | $C_{25}H_{19}NO_5$ | 72.57 (72.63) | 4.78 (4.63) | 3.33 (3.39) |
| 49 | H | ⌬—Me | ⌬—OMe | 175.5 | 90 | $C_{24}H_{19}NO_3$ | 78.31 (78.03) | 5.15 (5.18) | 3.91 (3.79) |
| 50 | H | ⌬—Cl | ⌬—OMe | 208 | 82 | $C_{23}H_{16}NO_3Cl$ | 70.90 (70.86) | 4.11 (4.14) | 3.47 (3.59) |
| 51 | H | —(CH₂)₅CH₃ | ⌬—OMe | oil | 85 | $C_{23}H_{25}NO_3$ | 75.99 (76.01) | 7.19 (6.93) | 3.87 (3.85) |
| 52 | H | 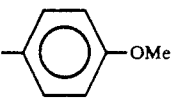 | ⌬—OMe | oil | 87 | $C_{23}H_{23}NO_3$ | 76.64 (76.43) | 6.54 (6.41) | 3.99 (3.88) |
| 53 | H | ⌬—OMe | —CH(CH₂CH₂CH₃)₂ | oil | 82 | $C_{24}H_{27}NO_3$ (¼ H₂O) | 74.65 (74.58) | 7.21 (7.30) | 3.42 (3.62) |
| 54 | 5-Cl | ⌬—OMe | ⌬—OMe | 238~240 | 80 | $C_{24}H_{18}NO_4Cl$ (¼ H₂O) | 67.65 (67.69) | 4.34 (4.42) | 3.09 (3.29) |
| 55 | 5-Me | ⌬—OMe | ⌬—OMe | 172~173 | 90 | $C_{25}H_{21}NO_4$ | 75.33 (75.17) | 5.33 (5.30) | 3.43 (3.51) |
| 56 | 5-OMe | ⌬—OMe | ⌬—OMe | 154~155 | 90 | $C_{25}H_{21}NO_5$ (¼ H₂O) | 71.36 (71.25) | 5.10 (5.18) | 3.18 (3.32) |

TABLE 2-continued

Structure: 3-(=CHR⁵)-indolin-2-one with R¹ on benzene ring and N-C(=O)R⁴

| No. | R¹ | R⁵ | R⁴ | m.p. (°C.) | yield (%) | formula | elementary analysis (%) C | H | N |
|---|---|---|---|---|---|---|---|---|---|
| 57 | H | 4-MeO-C₆H₄ | 2-MeO-C₆H₄ | 144.5~145.5 | 95 | C₂₄H₁₉NO₄ | 74.95 (74.79) | 5.39 (4.97) | 3.44 (3.63) |
| 58 | H | 4-MeO-C₆H₄ | 2-Cl-C₆H₄ | 133.5~134 | 83 | C₂₃H₁₆NO₃Cl | 70.86 (70.86) | 4.12 (4.14) | 3.50 (3.59) |
| 59 | H | 4-MeO-C₆H₄ | 4-pyridyl | 173~174 | 80 | C₂₂H₁₆N₂O₃ (1/5 H₂O) | 73.46 (73.40) | 4.52 (4.59) | 7.59 (7.78) |
| 60 | H | 4-MeO-C₆H₄ | 4-NEt₂-C₆H₄ | 64~65 (amorphous) | 80 | C₂₇H₂₆N₂O₃ (½ H₂O) | 74.37 (74.46) | 6.46 (6.25) | 6.37 (6.43) |
| 61 | H | 4-MeO-C₆H₄ | 4-OBn-C₆H₄ | 142~143 | 80 | C₃₀H₂₃NO₄ | 78.11 (78.08) | 5.18 (5.02) | 2.81 (3.03) |
| 62 | H | 4-MeO-C₆H₄ | 3-CF₃-C₆H₄ | 150~151 | 87 | C₂₄H₁₆NO₃F₃ | 68.07 (68.08) | 3.75 (3.81) | 3.27 (3.31) |
| 63 | H | 4-MeO-C₆H₄ | 3-CN-C₆H₄ | 180~181 | 82 | C₂₄H₁₆N₂O₃ | 75.58 (75.78) | 4.19 (4.24) | 7.38 (7.36) |
| 64 | H | 4-MeO-C₆H₄ | 3-NO₂-C₆H₄ | 201~202 | 85 | C₂₃H₁₆N₂O₅ | 68.85 (69.00) | 4.02 (4.03) | 6.97 (7.00) |
| 65 | H | 4-MeO-C₆H₄ | 4-Me-C₆H₄ | 204~205 | 95 | C₂₄H₁₉NO₃ | 78.05 (78.03) | 5.25 (5.18) | 3.73 (3.79) |
| 66 | H | 4-N(C₂H₅)₂-C₆H₄ | 4-OMe-C₆H₄ | oil | 85 | C₂₇H₂₆N₂O₃ (3H₂O) | 62.98 (62.72) | 5.68 (5.88) | 5.51 (5.42) |

TABLE 2-continued

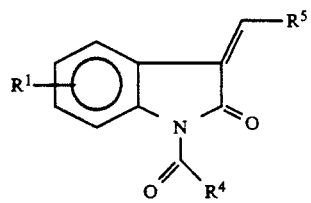

| No. | R¹ | R⁵ | R⁴ | m.p. (°C.) | yield (%) | formula | C | H | N |
|---|---|---|---|---|---|---|---|---|---|
| 67 | H | 4-CF₃-phenyl | 4-OMe-phenyl | 180~182 | 87 | $C_{24}H_{16}NO_3F_3$ (1/5 $H_2O$) | 67.54 (67.51) | 3.81 (3.87) | 3.26 (3.28) |
| 68 | H | 4-CN-phenyl | 4-OMe-phenyl | 203~205 | 85 | $C_{24}H_{16}N_2O_3$ (¼ $H_2O$) | 73.34 (73.46) | 4.18 (4.45) | 7.14 (7.14) |
| 69 | H | 3-NO₂-phenyl | 4-OMe-phenyl | 175~176 | 82 | $C_{23}H_{16}N_2O_5$ | 70.08 (69.90) | 4.17 (3.91) | 6.96 (6.79) |
| 70 | H | 4-pyridyl | 4-OMe-phenyl | 212~214 | 83 | $C_{22}H_{16}N_2O_3$ | 73.97 (74.15) | 4.35 (4.53) | 7.72 (7.86) |

TABLE 3

(solvent: CDCl₃)

| Compound No. | ¹H—NMR (δ, ppm) |
|---|---|
| 18 | 0.75~2.12(13H, m), 3.70(1H, br, t, J = 6.4 Hz), 3.87(3H, s), 6.89~7.81(8H, m) |
| 19 | 0.86~1.90(14H, m), 3.02(1H, dd, J = 12.9, 7.71 Hz), 3.34(1H, dd, J = 12.9, 5.1 Hz), 3.74(3H, s), 3.80(1H, m), 3.82(1H, dd, J = 7.71, 5.1 Hz), 6.66~7.28(8H, m) |
| 23 | 1.54(3H, s), 3.12(2H, s), 3.72(3H, s), 3.87(3H, s), 6.61~7.41(12H, m) |
| 24 | 2.84(1H, dd, J = 12.9, 8.2 Hz), 3.96(1H, dd, J = 12.9, 3.9 Hz), 3.75(3H, s), 3.78(3H, s), 3.80(1H, dd, J = 8.2, 3.9 Hz), 6.64~8.20(12H, m) |
| 25 | 2.93(1H, dd, J = 14.1, 9.0 Hz), 3.38(1H, dd, J = 9.0, 4.6 Hz), 6.70~8.30(12 H, m) |
| 28 | 3.14~3.40(2H, m), 3.77(3H, s), 3.84~4.04(1H, m), 6.60~8.88(12H, m) |
| 30 | 2.70(2H, brs), 2.84~3.36(2H, m), 3.76(3H, s), 3.90(1H, m), 6.68~8.00(12H, m) |
| 34 | 3.52(2H, m), 3.87(3H, s), 4.28(1H, m), 6.84~8.60(12H, m) |
| 51 | 0.72~1.80(11H, m), 2.64(2H, m), 3.87(3H, s), 6.89~7.83(9H, m) |
| 52 | 1.00~2.02(10H, m), 2.80~3.08(1H, m), 3.87(3H, s), 6.87~7.87(9H, m) |
| 53 | 0.78~1.96(14H, m), 3.89(3H, s), 4.08(1H, m), 6.94~8.35(9H, m) |
| 66 | 1.35(6H, t, J = 7.7 Hz), 3.52(4H, q, J = 7.7 Hz), 3.90(3H, s), 6.84~8.36(13H, m) |

TABLE 4

| | DOSE (mg/kg) | | | | | |
|---|---|---|---|---|---|---|
| | 1 | 3 | 10 | 30 | 100 | 300 |
| Compound 4 | | | 18 | 32 | 49 | |
| Compound 7 | 14 | 30 | 27 | 16 | 6 | |
| Compound 53 | 2 | 23 | 30 | 28 | 12 | |
| Aniracetam | | | 9 | 23 | 29 | 5 |

TEST EXAMPLE 2

Acute Toxicity Test

Mice (ddY, five-week-old males) were used in groups of 4 to 5 mice each. The test compound was dissolved or suspended in 0.5% solution of sodium carboxymethyl cellulose and administered orally. The mice were observed for 3 days to measure the number of deaths. Compound 1 was at least 4000 mg/kg in $LD_{50}$.

INDUSTRIAL APPLICABILITY

The medicaments for treating senile dementia must have cerebral function improving activity to ameliorate memory and learning disturbances and activity to activate the metabolism of cerebral nerve cells or to protect these cells from injuries and attacks. It is further desired that the medicaments be diminished in side effects and of high safety since the patients are aged people. When fulfilling these requirements, the medicaments are useful for treating senile dementia.

Table 4 reveals that the present compound exhibit antiamnesia activity and further have two activities, i.e., activity to improve cerebral functions and activity to activate cerebral metabolism or protect anoxic brain damage.

To sum up, the present compounds have two pharmacological activities, i.e., cerebral function improving activity and cerebral metabolism activating or anoxic brain damage protecting activity, low toxicity and therefore usefulness and are effective for treating senile dementia.

We claim:

1. An oxindole derivative represented by the formula

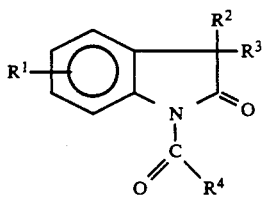

wherein $R^1$ is hydrogen atom, halogen atom, lower alkyl group or lower alkoxyl group, $R^2$ is hydrogen atom or lower alkyl group, $R^3$ is —$CH_2$—$R^5$ group, $R^5$ is lower alkyl; $C_{3-6}$ cycloalkyl, pyridyl, benzodioxanyl and phenyl optionally substituted with 1 to 3 substituents selected from the group consisting of halogen, lower alkyl, lower alkoxyl, hydroxyl, diethylamino, cyano, nitro, trifluoromethyl and benzyloxy, $R^2$ and $R^3$ may form together=CH—$R^5$ ($R^5$ being the same as above), $R^4$ is 1-propylbutyl group; pyridyl group; or phenyl group which may be substituted by lower alkoxyl group, halogen atom, diethylamino group, benzyloxy group, trifluoromethyl group, nitrile group, nitro group or lower alkyl group.

2. An oxindole derivative as defined in claim 1 wherein $R^1$ is hydrogen atom or lower alkoxyl group, $R^2$ is hydrogen atom, $R^3$ is —$CH_2$—$R^5$ group ($R^5$ being phenyl group which may have plural substituents selected from among halogen atom, lower alkyl group, lower alkoxyl group, hydroxyl group and diethylamino group), $R^4$ is 1-propylbutyl group, pyridyl group or phenyl group which may have plural lower alkoxyl groups as substituents.

3. An oxindole derivative as defined in claim 1 wherein $R^1$ and $R^2$ are each hydrogen atom, $R^3$ is —$CH_2$—$R^5$ group ($R^5$ being phenyl group substituted by 1 to 3 methoxy groups), $R^4$ is 4-methoxyphenol group or phenyl group.

4. An oxindole derivative as defined in claim 1 which is 1-(4-methoxybenzoyl)-3-(4-methoxybenzyl)oxindole.

5. An oxindole derivative as defined in claim 1 which is 1-(4-methoxybenzoyl)-3-(2,3,4-trimethoxybenzyl)oxindole.

6. A method of improving cerebral functions and activating cerebral metabolism or protecting anoxic brain damage characterized by administering to a patient an effective amount of the oxindole derivative of claim 1.

7. A pharmaceutical composition for the treatment of senile dementia comprising an effective amount of an oxindole derivative according to claim 1 and a pharmaceutically acceptable carrier.

* * * * *